United States Patent
DeCiccio et al.

(10) Patent No.: US 11,285,228 B2
(45) Date of Patent: Mar. 29, 2022

(54) METHOD AND APPARATUS FOR STERILIZED 3D PRINTING

(71) Applicant: Vitae Industries, Inc., Providence, RI (US)

(72) Inventors: Daniel John DeCiccio, Winter Park, FL (US); Jeanine Sinanan-Singh, Orlando, FL (US)

(73) Assignee: Vitae Industries, Inc., Providence, RI (US)

( * ) Notice: Subject to any disclaimer, the term of this patent is extended or adjusted under 35 U.S.C. 154(b) by 128 days.

(21) Appl. No.: 15/330,809

(22) Filed: Nov. 7, 2016

(65) Prior Publication Data

US 2017/0128601 A1 May 11, 2017

Related U.S. Application Data

(60) Provisional application No. 62/151,318, filed on Nov. 5, 2015.

(51) Int. Cl.
*A61L 2/10* (2006.01)
*B33Y 30/00* (2015.01)
(Continued)

(52) U.S. Cl.
CPC ...... *A61L 2/10* (2013.01); *A61L 2/22* (2013.01); *A61L 9/14* (2013.01); *A61L 9/20* (2013.01);
(Continued)

(58) Field of Classification Search
CPC ..... A61L 2/10; A61L 2/22; A61L 9/20; A61L 9/14; A61L 2202/24; A61L 2202/15;
(Continued)

(56) References Cited

U.S. PATENT DOCUMENTS

| | | | |
|---|---|---|---|
| 3,269,584 A * | 8/1966 | Ishida | B43K 5/14 |
| | | | 220/267 |
| 6,582,654 B1 * | 6/2003 | Kral | A61B 1/123 |
| | | | 134/161 |

(Continued)

OTHER PUBLICATIONS

Non-Final Office Action, U.S. Appl. No. 15/887,804 dated Feb. 19, 2021.

*Primary Examiner* — Timothy Kennedy
*Assistant Examiner* — Asha A Thomas
(74) *Attorney, Agent, or Firm* — Adler Pollock & Sheehan P.C

(57) ABSTRACT

An instrument produces clean and/or sterile products or compounds. The instrument includes a housing defining a clean interior. The housing has an inlet and a first HEPA filter for filtering an inflow through the inlet to create filtered air. A plurality of UV-C lights irradiate the interior. A 3D printer is in the interior to produce clean products. Preferably, the interior is CGMP compliant. The instrument may also have micro spray nozzles for spraying a sterilizing agent within the interior. A pressure pump can create a pressure differential, positive or negative, within the housing. Typically, the housing has an outlet with a second HEPA filter for filtering an outflow through the outlet to create environmentally safe air. An air circulator can create a laminar air flow through the housing.

16 Claims, 2 Drawing Sheets

(51) Int. Cl.
*B33Y 40/00* (2020.01)
*B33Y 10/00* (2015.01)
*B29C 64/35* (2017.01)
*A61L 9/20* (2006.01)
*A61L 2/22* (2006.01)
*A61L 9/14* (2006.01)

(52) U.S. Cl.
CPC .............. *B29C 64/35* (2017.08); *B33Y 10/00* (2014.12); *B33Y 30/00* (2014.12); *B33Y 40/00* (2014.12); *A61L 2202/11* (2013.01); *A61L 2202/122* (2013.01); *A61L 2202/15* (2013.01); *A61L 2202/21* (2013.01); *A61L 2202/24* (2013.01); *A61L 2209/134* (2013.01); *A61L 2209/14* (2013.01)

(58) Field of Classification Search
CPC .............. A61L 2202/11; A61L 2209/14; A61L 2209/134; A61L 2202/21; A61L 2202/122; B29C 64/35; B33Y 40/00; B33Y 10/00; B33Y 30/00
See application file for complete search history.

(56) References Cited

U.S. PATENT DOCUMENTS

| | | | |
|---|---|---|---|
| 2006/0111807 A1 | 5/2006 | Gothait et al. | |
| 2012/0308214 A1* | 12/2012 | Tyburk | F24F 13/20 392/407 |
| 2015/0217514 A1* | 8/2015 | Maier | B29C 64/255 264/241 |
| 2015/0301524 A1* | 10/2015 | Flitsch | G05B 19/4189 700/112 |
| 2015/0375453 A1* | 12/2015 | Yost | B29C 64/386 435/174 |
| 2016/0068793 A1* | 3/2016 | Maggiore | C12M 21/08 435/289.1 |
| 2018/0326665 A1* | 11/2018 | Gatenholm | B01L 1/02 |

* cited by examiner

METHOD AND APPARATUS FOR STERILIZED 3D PRINTING

CROSS-REFERENCE TO RELATED APPLICATION

This application claims priority to U.S. Provisional Patent Application No. 62/251,318, filed Nov. 5, 2015, which is incorporated herein by reference.

BACKGROUND OF THE INVENTION

1. Field of the Invention

The subject disclosure relates to methods and systems for 3D printing, and more particularly to improved methods and systems for 3D printing that are self-contained, sterile and/or capable of maintaining best manufacturing processes.

2. Background of the Related Art

Additive manufacturing, more commonly known as 3D printing, has become an increasingly popular method for the rapid prototyping and fabrication of a wide variety of products. 3D printers are now widely available to the general public due to recent low-cost models. One area of increased interest in 3D printing is the medical field where rapid and custom production can greatly benefit patients. Recently, the first 3D printed drug, Spritam levetiracetam, was FDA approved. 3D printed implants have been used in a wide variety of application from stents to cartilage replacement.

When producing medical products, maintaining a sterile working environment is key to eliminating contamination and infection. 3D printed implants must be sterilized after production using common techniques such as autoclaves, ethylene oxide chambers, solvent washes etc. 3D printed drugs must be produced in a sterile room or sterile environment to minimize contamination. The need for a sterilized working environment is a limitation which prevents use of 3D printed bioproducts outside of facilities already designed to handle such sterile working conditions. For example, a rural clinic or small medical practice may not be able to safely 3D print urgent medical products like custom drugs, compounds or custom implants including teeth and emergency stents.

Although some 3D printers may be used under a vacuum hood for filtration of fumes and or particulate contaminates created during the printing processes, current models fail to create and maintain a highly clean environment for manufacturing.

SUMMARY OF THE INVENTION

The subject technology is directed to a method and apparatus for creating medical products and compounds via 3D printing in a reliably sterile environment regardless of the presence of sterile facility.

In one embodiment, the subject technology is directed to an instrument for producing clean and/or sterile products. The instrument includes a housing defining a clean interior. The housing has an inlet and a first HEPA filter for filtering an inflow through the inlet to create filtered air. A plurality of UV-C lights irradiate the interior. A 3D printer is in the interior to produce clean products. Preferably, the interior is CGMP compliant. The instrument may also have micro spray nozzles for spraying a sterilizing agent within the interior. A pressure pump can create a pressure differential, positive or negative, within the housing. Typically, the housing has an outlet with a second HEPA filter for filtering an outflow through the outlet to create environmentally safe air. An air circulator can create a laminar air flow through the housing.

The instrument may also have a sterile internal needle having an extrusion tip and a septum, wherein: the extrusion tip is operable to puncture the septum; and the sterile internal needle is operable to draw at least one sterile working material into the sterile interior. A plurality of replacement extrusion tips can be stored in the interior or in a similarly convenient location. The 3D printer includes sterile components. Further, the sterile interior, the HEPA filters, and the plurality of UV-C lights may be selectively coated with a sterilizable material. The sterilizable material is selected from the group consisting of: ceramic; metals; and polymers. Aluminum, polycarbonate, polyacrylamide, polyacrylic and the like are possible sterilizable materials.

Another embodiment of the subject technology is directed to a method for creating sterile pharmaceutical compounds from at least one component including the steps of: creating a work station by enclosing a 3D printer within an interior of a housing; filtering air for filling the interior; flooding the interior station with UV-C light; and producing a sterile pharmaceutical compound within the work station using the 3D printer. The interior of the housing and 3D printer may be sterilized by the UV-C light. To further sterilize the work station, the method may mist a sterilizing agent over the interior of the work station. Filtered air is preferably circulated within the interior in a laminar pattern. The method may also include sterilizing and curing at least one component of the product by using one of the following: heat; or UV-C light.

The method may also include the steps of: forming a septum in a portion of the work area; puncturing the septum with a sterile internal needle, the sterile internal needle having a sterile extrusion tip; and drawing material into the working area using the sterile internal needle. The method also can include the steps of: storing at least one sterilized replacement tip in the work area; and after drawing material into the working area using the sterile internal needle, replacing the sterile extrusion tip with one of the sterilized replacement tips.

Still another embodiment of the subject technology is directed to an instrument for producing sterile products including an inner chamber having a 3D printer, a pressure pump, a sterile internal needle, a septum, an air circulator, and a micro spray nozzle connected to a spray pump. A first outer chamber fluidly connects to the inner chamber. The first outer chamber includes: an inlet, a HEPA filter, and a UV-C light. A second outer chamber fluidly connects to an inner chamber. The second outer chamber includes: an outlet, a HEPA filter, and a UV-C light. One or more UV-C lights irradiate at least the inner chamber. Preferably, air within the inner chamber flows in a laminar pattern between the first outer chamber and the second outer chamber, and the pressure pump maintains a positive pressure within the inner chamber.

It should be appreciated that the subject technology can be implemented and utilized in numerous ways, including without limitation as a process, an apparatus, a system, a device, a method for applications now known and later developed or a computer readable medium. These and other unique features of the system disclosed herein will become more readily apparent from the following description and the accompanying drawings.

BRIEF DESCRIPTION OF THE DRAWINGS

So that those having ordinary skill in the art to which the disclosed system appertains will more readily understand how to make and use the same, reference may be had to the following drawings.

DETAILED DESCRIPTION OF PREFERRED EMBODIMENTS

Figure 1:
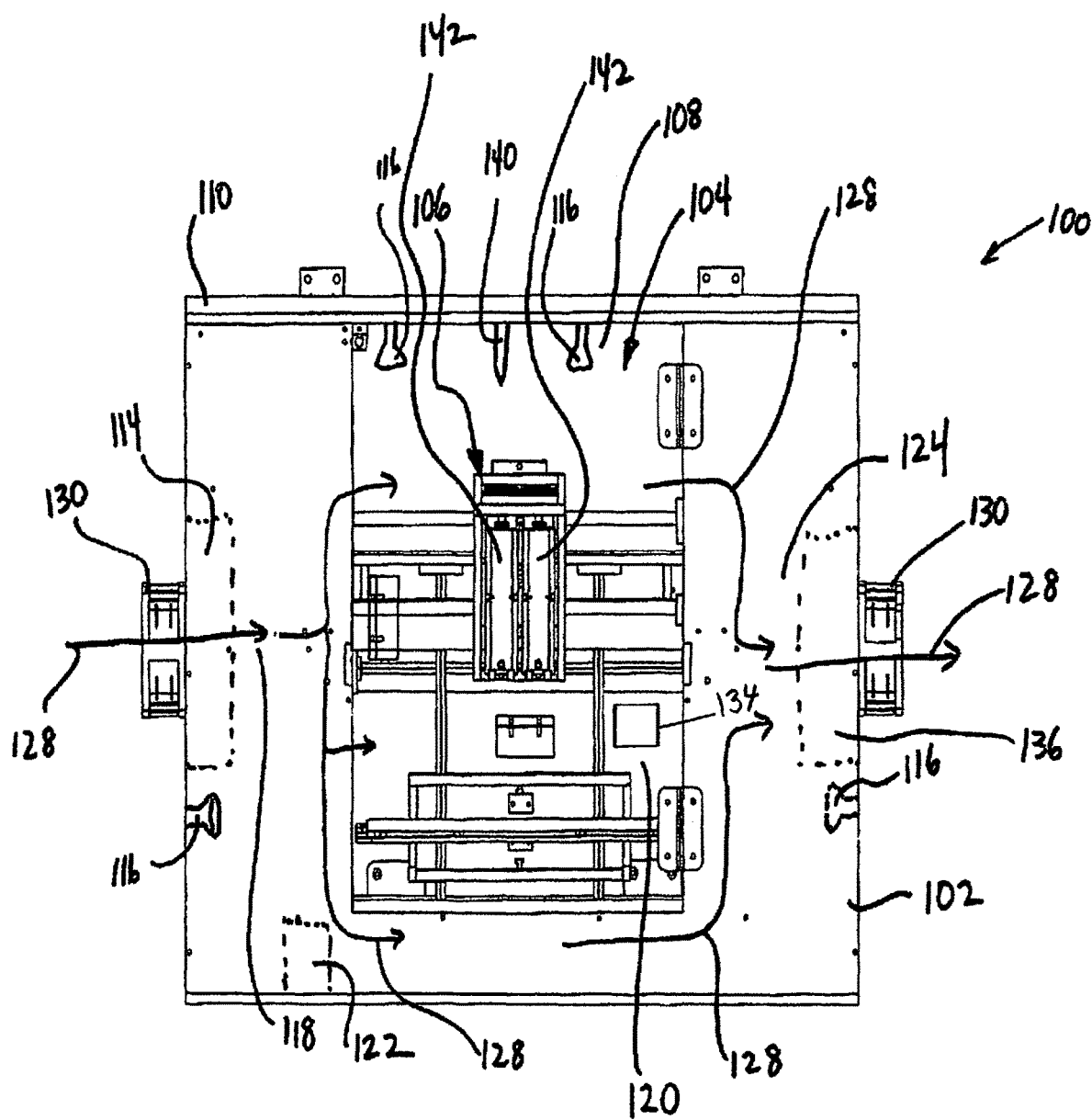
FIG. 1 is a front view of an instrument for producing sterile products in accordance with the subject disclosure.
Figure 2:
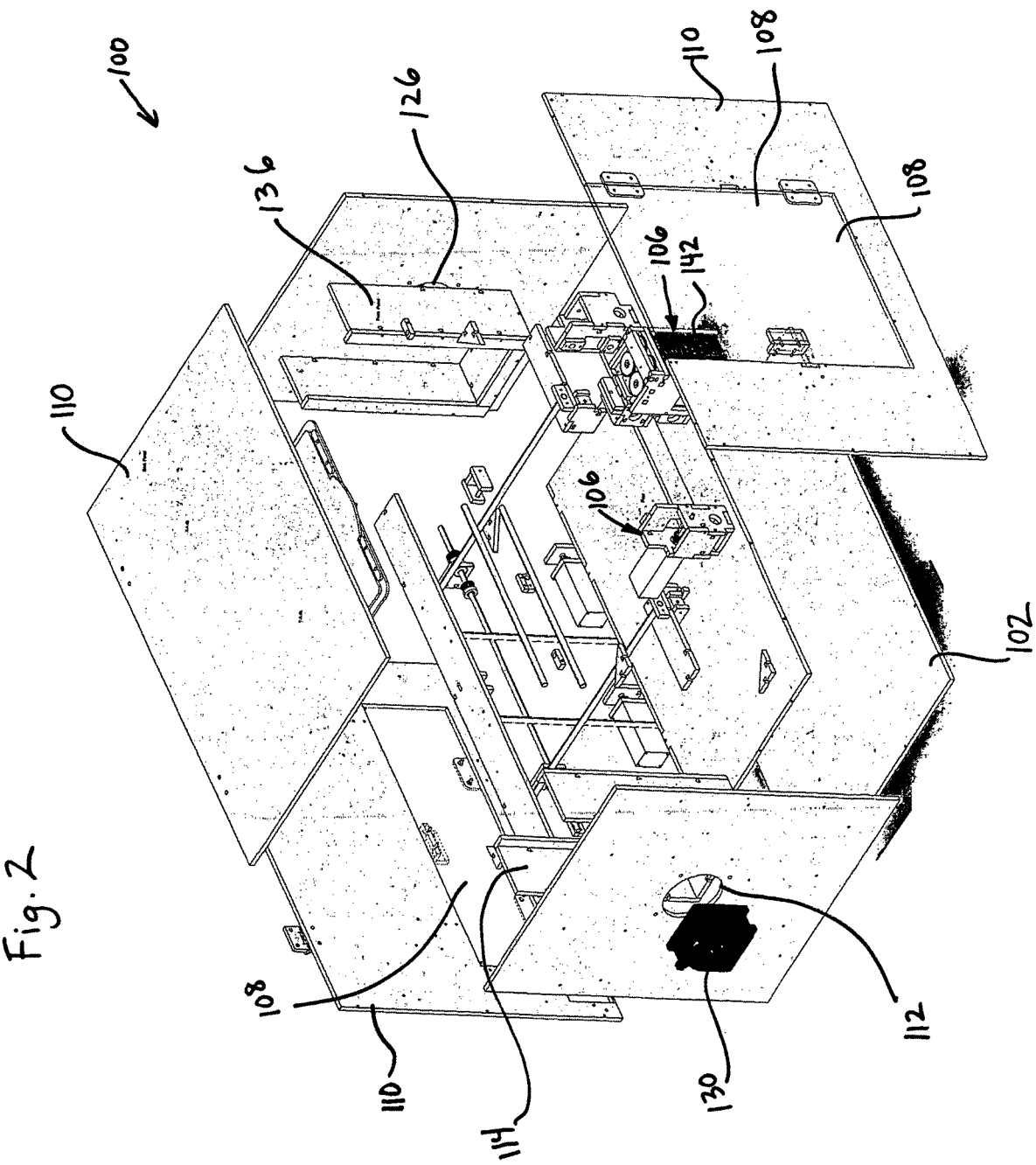
FIG. 2 is an exploded view of the instrument of FIG. 1.

The subject technology overcomes many of the prior art problems associated with producing sterile items fabricated using 3D printing. The advantages, and other features of the systems and method disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

In brief overview, the 3D printer of the subject disclosure is a fully self-contained unit, which allows sterile production of medical products without any additional outside matter. Primary ways in which a sterile internal environment/working area is maintained are described in more detail below. The attached Figures and following description provide illustration of embodiments of the subject technology.

Referring now to FIG. 1, an instrument for producing sterile products in accordance with the subject disclosure is shown generally at 100. The instrument 100 includes a housing 102 which defines a sterile interior 104. The sterile interior 104 is used, in whole or in part, as a work station for creating the sterile product. To that end, a 3D printer 106 is included within the sterile interior 104 and is operable to produce sterile products. The housing 102 has one or more windows 108 for visual access to the interior 104. The windows 108 and panels 110 of the housing 102 may be hingedly connected and/or permanently fixed together.

The instrument 100 also includes an inlet 112 which draws air through a first high efficiency particulate arrestance (hereinafter HEPA) filter assembly 114, creating filtered air (not distinctly shown). Additional HEPA filters can be added to provide greater filtration or to increase the length of time before it becomes necessary to replace the filters. Additionally, UV-C lights 116 irradiate the sterile interior 104 of the instrument 100. The UV-C lights 116 improve sterilization by destroying and/or sterilizing pathogens such as bacteria, viruses, mold spores, cysts and the like. By irradiating the sterile interior 104, the UV-C lights 116 sterilize the air within the sterile interior 104 as well as the equipment within the sterile interior 104 such as the 3D printer 106.

In the embodiment shown, air entering through the inlet 112 is filtered through a HEPA filter assembly 114 and irradiated by UV-C lights 116 in a first outer area or chamber 118. Only after the air is filtered and irradiated in the first outer chamber 118 is the filtered air then circulated into an inner area or chamber 120 that includes the 3D printer 106. In other words, the external air is filtered and sanitized before introduction to the inner chamber 120 of the system 100. In this way, the inner chamber 120 can be used as a substantially sterile work station.

Further, an air circulator 122 causes the filtered and sterilized air to continuously move in a laminar pattern within the system 100 to minimize the chance of contamination while the unit is both idle and operating. For example, the air circulator 122 can move the air in a laminar pattern from top to bottom or side to side. Preferably, the laminar pattern moves the filtered air from the first outer chamber 118 to the inner chamber 120 to a second outer area or chamber 124 for egress from an outlet 126 as shown by flow arrows 128. Fans 130, mounted on the inlet 112 and outlet 126 respectively, help establish the laminar pattern. A second HEPA filter assembly 136 is also mounted on the outlet 126.

By continually moving air throughout the instrument 100 in a laminar pattern, the air circulator 122 and fans 130 limit the potential for unfiltered air to enter the inner chamber 120. Further, by recirculating air within the system 100, such as sending filtered and sanitized air from the second outer chamber 124 back into the first outer chamber 118, air inside the system 100 can also be recirculated to reduce sanitization needs. The inner chamber 120 is also equipped with one or more pressure pumps 134 which can maintain a positive or negative pressure in the sterile interior 104 as desired. A positive pressure differential can further limiting the potential for unfiltered outside air to enter. A negative pressure differential can further limit outgas and the like from the interior. Alternatively, the system 100 can be sealed with an internal laminar flow.

Air within the inner chamber 120 may, in some cases, be contaminated by the 3D printing process. Therefore, it may be desirable to filter and/or sterilize contaminated air within the system 100, either before the air is recirculated into the system 100, or before the air is reintroduced into the outside environment. Therefore, the second outer chamber 124 includes the second HEPA filter assembly 136 and UV-C light 116, for filtering and sterilizing air within the second outer chamber 124. In this way, the instrument can create filtered, sterilized air that is safe for recirculating within the instrument. It is envisioned that the outer chambers 118, 124 can be arranged in a variety of configurations depending upon the application. Additionally, the HEPA filter assemblies 114, 136 remove noxious fumes to create safe air for reintroduction into the outside environment via the outlet 126.

In one embodiment, the UV-C lights 116 are mounted over and under the working area to guarantee all surfaces can be sufficiently irradiated. In effect, the UV-C light guarantees there are no live pathogens on any of the working surfaces before fabrication. The UV-C lights 116 can also be used to cure/set uv-sensitive polymers and other materials as part of the 3D printing process. UV-C lights are commonly used and widely accepted/certified for medical sanitation of surfaces as well as water/air purification. The ability to sterilize the unit before construction allows a user to open the window 108 of the system 100, remove parts, perform maintenance and the like, then have the interior 104 sterilized and ready to use quickly.

The system 100 also includes a micro spray nozzle 140 for spraying a sterilizing agent within the sterile interior 104. The sterilizing agent can be hydrogen peroxide as an alternative or second level of protection for initial sterilization of the interior 104. A mist of sterilizing agent may be automatically sprayed over all surfaces from centrally located nozzles. After a short amount of time (e.g., less than 60 minutes), all surfaces would be sterile.

Air filtration and direction is another aspect addressed by the subject technology. HEPA (high efficiency particulate arrestance) filters which can be combined with additional UV-C lights supply clean air to the system and sterilize surfaces. In other words, the external air is filtered and sanitized before introduction to the work area of the system 100. Already sterile air from inside the system 100 can also be recirculated to reduce sanitization needs. The filtered and sterilized air continuously moves in a laminar pattern within the system to minimize the change of contamination while the unit is both idle and operating. Filtration also serves to remove any noxious fumes and contain such fumes in the system.

In one embodiment, the system 100 has an air-tight seal such as a tightly fitted housing 102 to prevent external contamination from entering. In another embodiment, an air-tight seal from the outside world is not practical. Positive pressure is maintained within in the system 100 to limit the possibility of contaminants entering the system 100. The system 100 maintains a slight higher pressure within to prevent contamination from entering. Both positive pressure and laminar flow are currently used in clean rooms and some operating rooms to ensure sterile working areas. The 3D printer of the subject technology has the positive pressure and laminar flow built in so that parts are produced in a sterile environment.

The system 100 carefully introduces the sterile working materials. The materials the 3D printer uses to manufacture products are sterile to help the resulting product produced to be sterile. For example, the 3D printer 106 may use cartridges 142 that contain sterile ingredients for the resulting products. In a drug compounding application, the cartridges are pre-filled and FDA approved so that more common local pharmacies can utilize the subject technology to produce drug compounds with requiring a full drug compounding facility. Another application is cartridges with medical cannabis for approved dispenseries to create a variety of 3D printed products on site. The subject technology is significantly more advantageous as by producing the product in a sterile environment with sterile cartridges, subsequent sterilization is not needed.

Contaminated components may be sterilized by the manufacturing process due to application of heat (e.g., heat lamps), the UV light, the process needed to extrude or cure the products, and/or the sterile misting and the like. In the case of heated extruded material, if the material is not already sterile, it would need to be heated to appropriate temperatures during extrusion for sterility. The 3D printer may include a heating assembly or the heat could be delivered from a secondary source such as warmed laminar flow. The laminar flow assists with carrying away particulate contaminants created during the heating/extrusion process so that the particulate contaminants are not incorporated in the product. Unsterile working materials will be held in a separate area of the devices which is sealed off to prevent contamination of sterile environments.

Sterile working materials can also be efficiently incorporated into the work area. In one embodiment, the sterile working material arrives. The working material is drawn into the working area by a sterile internal needle puncturing a septa or dividing wall and drawing the clean material into the sterile working area. The tools/tips/needs (e.g., needle) and septa can be sterilizable through techniques including but not limited to the aforementioned techniques or replaceable. In the case of disposable tips, sterile extrusion tips (such as syringe or micropipette tips which are shipped sterile) will be stored within the system's clean and sterilized area. After one tip is finished, the 3D printer can automatically dispose of the used tip and insert a new tip as needed. Preferably, materials within the working area are made of or coated with a material which can be readily sterilized such as ceramic, metals or certain polymers. Additional sterilization techniques such as autoclave or like functionality where heat and pressure ensure sterilization can also be employed to sterilize the working area and components before and after use.

It is envisioned that the subject technology results in a work environment that is Current Good Manufacturing Practice (CGMP) regulations compliant as set forth by the US Food and Drug Administration (FDA). As CGMP are modified, the subject technology can be adapted to maintain CGMP processes and facilities.

As can be seen from review of the above, built in, self-contained sterilization allows 3D printers to be used in almost any environment and still produce medically usable products. In the case of 3D printed drugs, even a small business or pharmacy could produce pharmaceutical quality products. Pharmaceutical companies do not need to produce products in clean rooms because the clean room is built in to the 3D printer allowing the same cleanliness standards to be achieved. For the production of implants, surgeons and patients would be able to know a product that is produced on demand is as clean as any traditionally produced and sterilized implant.

It will be appreciated by those of ordinary skill in the pertinent art that the functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, databases, interfaces, computers, servers and the like) shown as distinct for purposes of illustration may be incorporated within other functional elements in a particular implementation.

While the subject technology has been described with respect to preferred embodiments, those skilled in the art will readily appreciate that various changes and/or modifications can be made to the subject technology without departing from the spirit or scope of the invention as defined by the appended claims.

What is claimed is:

1. An instrument for producing clean products comprising:
   a housing of the instrument defining a clean interior for human pharmaceuticals, the housing having an inlet;
   an inner chamber configured as a sterile work station;
   a first outer chamber fluidly connected to the inner chamber and configured to filter and irradiate air;
   a second outer chamber fluidly connected to an inner chamber and configured to filter and irradiate air;
   a first HEPA filter for filtering an inflow through the inlet to create filtered air;
   a plurality of UV-C lights within the clean interior for irradiating the clean interior of the housing;
   a 3D printer enclosed in the inner chamber of the clean interior of the housing operable to produce clean products;
   a sterile needle enclosed in the clean interior, the sterile internal needle having an extrusion tip and a septum, the extrusion tip operable to puncture the septum and the sterile internal needle operable to draw at least one sterile working material into the clean interior; and
   a plurality of replacement extrusion tips.

2. The instrument of claim 1, further comprising at least one micro spray nozzle for spraying a sterilizing agent within the interior.

3. The instrument of claim 1, further comprising a pressure pump for creating a pressure differential within the housing.

4. The instrument of claim 1, wherein the housing has an outlet.

5. The instrument of claim 4, further comprising a second HEPA filter for filtering an outflow through the outlet to create environmentally safe air.

6. The instrument of claim 1, further comprising an air circulator for creating a laminar air flow through the housing.

7. The instrument of claim 1, wherein the 3D printer comprises a plurality of sterile components.

8. The instrument of claim 7, wherein the clean interior, the first HEPA filter, and the plurality of UV-C lights are coated with a sterilizable material.

9. The instrument of claim 8, wherein the sterilizable material is chosen from one of the following: ceramic; metals; or polymers.

10. An instrument comprising:
- a housing that defines a sterile interior, the sterile interior including an enclosed 3D printer, enclosed UV-C lights and a micro spray nozzle, the housing including one or more windows for visual access to an interior;
- an inner chamber configured as a sterile work station;
- a first outer chamber fluidly connected to the inner chamber and configured to filter and irradiate air;
- a second outer chamber fluidly connected to an inner chamber and configured to filter and irradiate air;
- an inlet that draws air through a first high-efficiency particulate air filter assembly;
- a sterile needle enclosed in the sterile interior, the sterile internal needle having an extrusion tip and a septum, the extrusion tip operable to puncture the septum and the sterile internal needle operable to draw at least one sterile working material into the sterile interior;
- an air circulator that causes filtered air to continuously move in a laminar pattern; and
- one or more pressure pumps.

11. The instrument of claim 10 wherein the one or more windows are hingedly connected.

12. The instrument of claim 10 wherein the one or more windows are permanently fixed together.

13. The instrument of claim 10 wherein the inlet draws air through a second high-efficiency particulate air filter assembly.

14. The instrument of claim 10 wherein the air circulator is supplemental with one or more fans.

15. The instrument of claim 10 wherein the micro spray nozzle is configured to spray a mist of a sterilizing agent.

16. The instrument of claim 10 wherein the sterilizing agent is hydrogen peroxide.

* * * * *